(12) United States Patent
Hayakawa et al.

(10) Patent No.: US 11,173,647 B2
(45) Date of Patent: Nov. 16, 2021

(54) HEATING APPARATUS FOR PREFORMS AND HEATING METHOD FOR PREFORMS

(71) Applicant: Dai Nippon Printing Co., Ltd., Tokyo (JP)

(72) Inventors: Atsushi Hayakawa, Tokyo (JP); Yuiko Wada, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 16/623,956

(22) PCT Filed: Jun. 20, 2018

(86) PCT No.: PCT/JP2018/023410
§ 371 (c)(1),
(2) Date: Dec. 18, 2019

(87) PCT Pub. No.: WO2018/235850
PCT Pub. Date: Dec. 27, 2018

(65) Prior Publication Data
US 2020/0139608 A1 May 7, 2020

(30) Foreign Application Priority Data

Jun. 23, 2017 (JP) .............................. JP2017-122808

(51) Int. Cl.
*B29C 49/68* (2006.01)
*B29C 49/46* (2006.01)
(Continued)

(52) U.S. Cl.
CPC .............. *B29C 49/68* (2013.01); *B29C 49/06* (2013.01); *A61L 2202/23* (2013.01);
(Continued)

(58) Field of Classification Search
CPC ................ B29C 49/46; B29C 49/6409; B29C 2049/4679; B29C 2049/4697; B29C 49/36; B29C 49/68
(Continued)

(56) References Cited

U.S. PATENT DOCUMENTS 4,836,971 A * 6/1989 Denis .................... B29C 49/649
264/342 R
5,032,700 A * 7/1991 Sugiyama ............... B29C 35/08
219/601
(Continued)

FOREIGN PATENT DOCUMENTS

EP 0202973 A1 * 11/1986 ......... B29C 71/0063
JP H06-015645 A1 1/1994
(Continued)

OTHER PUBLICATIONS

Partial translation of Bit (EP 0 202 973 A1) dated Nov. 1986, obtained from the espace website. (Year: 1986).*
(Continued)

*Primary Examiner* — Robert B Davis
(74) *Attorney, Agent, or Firm* — Burr & Brown, PLLC

(57) ABSTRACT

A heating apparatus and a heating method for preforms are provided which eliminate poor sterilization of a mouth portion of a preform to which a disinfectant has been blown. The heating apparatus includes a heating section that heats the preform is provided with a mouth portion heating section, and a mouth portion of the preform is heated to a temperature in a range of 50° C. to 70° C.

8 Claims, 8 Drawing Sheets

(51) Int. Cl.
*B29C 49/06* (2006.01)
*B29C 35/08* (2006.01)
*B29K 67/00* (2006.01)
*B29K 105/00* (2006.01)
*B29L 31/00* (2006.01)

(52) U.S. Cl.
CPC .. *B29C 2035/0822* (2013.01); *B29K 2067/00* (2013.01); *B29K 2105/258* (2013.01); *B29L 2031/7158* (2013.01)

(58) Field of Classification Search
USPC .......................................................... 264/908
See application file for complete search history.

(56) References Cited

U.S. PATENT DOCUMENTS

| | | | |
|---|---|---|---|
| 5,308,233 | A | 5/1994 | Denis et al. |
| 5,322,651 | A | 6/1994 | Emmer |
| 5,681,521 | A | 10/1997 | Emmer et al. |
| 2006/0157896 | A1* | 7/2006 | Lee ............... B29C 49/6409 264/345 |
| 2008/0015253 | A1 | 6/2008 | Quetel et al. |
| 2016/0075075 | A1 | 3/2016 | Pollmann-Retsch et al. |
| 2016/0207245 | A1 | 7/2016 | Lewin et al. |
| 2016/0257055 | A1* | 9/2016 | Hayakawa ............... A61L 2/06 |
| 2016/0263269 | A1 | 9/2016 | Hayakawa et al. |
| 2018/0009646 | A1 | 1/2018 | Hayakawa et al. |

FOREIGN PATENT DOCUMENTS

| | | |
|---|---|---|
| JP | H08-504699 A1 | 5/1996 |
| JP | 2008-183899 A1 | 8/2008 |
| JP | 2008-198571 A1 | 8/2008 |
| JP | 2015-116814 A1 | 6/2015 |
| JP | 2016-516616 A1 | 6/2016 |
| JP | 2016-120597 A1 | 7/2016 |
| JP | 2016-137629 A1 | 8/2016 |
| JP | 2017-074705 A1 | 4/2017 |
| JP | 2017-100353 A1 | 6/2017 |
| WO | 2006/011201 A1 | 2/2006 |
| WO | WO-2015072506 A1 * | 5/2015 ............... A61L 2/06 |
| WO | 2016/104410 A1 | 6/2016 |

OTHER PUBLICATIONS

International Search Report and Written Opinion (Application No. PCT/JP2018/023410) dated Sep. 18, 2018.
Extended European Search Report, European Application No. 18821412.6, dated Jan. 28, 2021 (9 pages).

* cited by examiner

SUPPLY OF PREFORM

BLOWING OF DISINFECTANT GAS

BLOW MOLDING

REMOVAL OF BOTTLE

HEATING APPARATUS FOR PREFORMS AND HEATING METHOD FOR PREFORMS

FIELD OF THE INVENTION

The present invention relates to a heating apparatus for preforms that sterilizes a preform and heats the sterilized preform, and a heating method for preforms.

BACKGROUND OF THE INVENTION

Biaxially stretched polyethylene terephthalate (PET) bottles widely used as containers for drinks or the like are suitable for mass production. A biaxially stretched PET bottle is produced by heating an injection-molded preform to a molding temperature and then blow-molding the preform. The blow-molded bottle is filled with a content and then sealed with a cap by fitting the cap to the opening of the bottle, which is formed when the preform is injection-molded. If the mouth portion is deformed when the preform is being heated, the sealing by the cap is compromised after the cap is fitted. For this reason, the mouth portion should not be excessively heated. To prevent the mouth portion of the preform from being deformed by the heat when the preform is heated, a heating apparatus for preforms is provided with a protection body cooled by a flow of water that prevents the mouth portion of the preform from being excessively heated by the near infrared radiation emitted by a heating element (Patent Literature 1). In order to mold the preform into the bottle, the heating temperature for the part of the preform excluding the mouth portion that is to form the body of the molded bottle needs to be equal to or higher than the glass transition temperature of the thermoplastic resin forming the preform (Patent Literature 2). In other words, in order to prevent the mouth portion of the preform from being deformed, the temperature of the mouth portion of the preform during heating of the preform must not be equal to or higher than the glass transition temperature of the thermoplastic resin forming the mouth portion.

There are aseptic filling machines that combine a blow molding machine that molds a preform into a bottle and a filling apparatus that fills the bottle with a content such as a drink and performs the filling in an aseptic atmosphere, rather than separately performing a step of molding a preform into a bottle and a step of filling the molded bottle with a content. Today, most drink products are manufactured by such aseptic filling machines.

As an aseptic filling machine, an apparatus has been proposed which sprays a disinfectant to a preform while the preform is continuously traveling, introduces the preform into a heating furnace, heats the preform to a temperature for molding the preform into a container in the heating furnace, and dries and activates the disinfectant sprayed to the preform at the same time by the heating (Patent Literature 3). With such an apparatus, the disinfectant on the preform is activated in the heating furnace, and the preform is sterilized in the heating furnace. Therefore, the mouth portion of the preform is preferably heated to a temperature at which the disinfectant is activated. However, in order to prevent deformation of the mouth portion of the preform caused by overheating, the mouth portion of the preform is protected from the infrared radiation by a cooled inclined plate.

Further, a drink filling method has been proposed which involves blowing a mist or gas of a hydrogen peroxide solution to a preform, removing the hydrogen peroxide adhering to the surface of the preform, heating the preform to a molding temperature, molding the preform at the molding temperature into a bottle in a blow-molding die that is also continuously traveling, removing the bottle from the blow-molding die, filling the bottle with a drink and then sealing the bottle with a cap (Patent Literature 4). In this method, again, the part of the preform that is to form the body of the molded bottle is heated to a temperature from 90° C. to 130° C., although the temperature of the mouth portion of the preform is kept to be equal to or lower than 70° C. in order to prevent deformation or the like of the mouth portion of the preform.

CITATION LIST

Patent Literature

Patent Literature 1: Japanese Patent Laid-Open No. 6-15645
Patent Literature 2: Japanese Patent Laid-Open No. 8-504699
Patent Literature 3: Japanese Patent Laid-Open No. 2008-183899
Patent Literature 4: Japanese Patent Laid-Open No. 2015-116814

SUMMARY OF THE INVENTION

Technical Problem

Conventional aseptic filling machines for bottles molds a preform into a bottle and sterilizes the molded bottle. Such aseptic filling machines require a vast amount of disinfectant and tend to be too large in size. Thus, aseptic filling machines that sterilize preforms are becoming popular. With such aseptic filling machines, as described in Patent Literatures 3 and 4 described above, the preforms are sterilized by blowing a gas or mist of a hydrogen peroxide solution or a mixture thereof to the preforms. Once the gas or mist of the hydrogen peroxide solution or the mixture thereof is blown to the preforms, heated aseptic air is blown to the preforms to remove the hydrogen peroxide solution and activate the hydrogen peroxide to sterilize the preforms (Patent Literature 4). However, the gas or mist of the hydrogen peroxide solution or the mixture thereof may remain on the preforms to which it has been blown, and the preforms may be further sterilized by the gas or mist or the mixture thereof when the preforms are heated to the molding temperature.

Although the other parts of the preform than the mouth portion are heated to a temperature from 90° C. to 130° C., the temperature of the mouth portion must be kept to be equal to or lower than 70° C. in order to prevent deformation of the mouth portion caused by overheating. In practice, however, the temperature is sometimes 40° or less, and the mouth portion is hardly sterilized in the heating. Further, according to Patent Literature 3, a vapor of a hydrogen peroxide solution is blown to the preform, and then the preform is directly heated. In this case, the hydrogen peroxide is activated by the heat in the heating to sterilize the preform. However, the mouth portion of the preform is isolated from the heat that heats the body of the preform by the cooled inclined plate that prevents overheating of the mouth portion of the preform. As a result, the mouth portion is not heated and can be poorly sterilized.

With the aseptic filling machine that sterilizes a preform by blowing a disinfectant to the preform, the heating temperature of the mouth portion of the preform has to be kept low, and as a result, the temperature of the mouth portion is not sufficiently raised, and the mouth portion can be insufficiently sterilized. There is a demand for an aseptic filling machine that properly heats the mouth portion of a preform and prevents poor sterilization of the mouth portion and an aseptic filling method therefor.

An object of the present invention is to provide a heating apparatus for preforms in an aseptic filling machine for sterilizing preforms and a heating method for preforms in which an mouth portion of a preform is heated to a temperature equal to or lower than a deformation temperature and equal to or higher than a sterilization temperature when the preform is heated to a molding temperature after a disinfectant is blown to the preform.

Solution to Problem

A heating apparatus for preforms according to the present invention is a heating apparatus for preforms that heats a preform to a temperature for blow-molding the preform into a bottle, the heating apparatus comprising an mouth portion heating section that heats an mouth portion of the preform, and a body portion heating section that heats a body portion of the preform, wherein the mouth portion heating section includes mouth portion heating equipment that heats the mouth portion to a temperature from 50° C. to 70° C.

In the heating apparatus for preforms according to the present invention, the body portion heating section preferably includes body portion heating equipment that heats the body portion to a temperature from 90° C. to 140° C.

In the heating apparatus for preforms according to the present invention, the mouth portion heating section is preferably provided in an early stage in the heating apparatus.

In the heating apparatus for preforms according to the present invention, the mouth portion heating equipment preferably includes a halogen lamp and a condenser that collects near infrared radiation emitted from the halogen lamp to the mouth portion.

A heating method for preforms according to the present invention is a heating method for preforms in which a preform to which a disinfectant containing hydrogen peroxide has been blown is heated to a temperature for blow-molding the preform into a bottle, wherein a mouth portion of the preform is heated to a temperature from 50° C. to 70° C.

In the heating method for preforms according to the present invention, a body portion of the preform is preferably heated to a temperature from 90° C. to 140° C.

In the heating method for preforms according to the present invention, the heating of the mouth portion is preferably achieved by collecting near infrared radiation emitted from a halogen lamp to the mouth portion of the preform.

Advantageous Effects of the Invention

With the heating apparatus for preforms and the heating method for preforms according to the present invention, when a preform in contact with a disinfectant is heated to a molding temperature for molding the preform into a bottle, the preform can be heated to a proper temperature at which a mouth portion of the preform is not deformed. As a result, the sterilization of the mouth portion of the preform can be improved, and poor sterilization of the mouth portion of the preform can be eliminated. In particular, the heating apparatus and the heating method are effective in sterilizing a preform by bringing a gas or mist of a hydrogen peroxide solution or a mixture thereof into contact with the preform.

An aseptic filling machine having a sterilization unit that sterilizes a preform in such a manner can ensure high sterility if the aseptic filling machine is provided with the heating apparatus for preforms according to the present invention.

DETAILED DESCRIPTION OF THE INVENTION

In the following, an embodiment of the present invention will be described with reference to the drawings.

In an aseptic filling machine incorporating a heating apparatus for preforms according to the present invention, a preform supplied from a preform supplying apparatus is sterilized in a sterilizing unit, and the sterilized preform is heated by a heating apparatus for preforms according to the present invention to a temperature at which the preform can be molded into a bottle. A summary of the heating apparatus for preforms and a heating method for preforms according to the present invention will be described with reference to FIG. 1, which shows apart of the aseptic filling machine incorporating the heating apparatus according to the present invention, and then the heating apparatus for preforms will be described in detail with reference to FIGS. 5, 6, 7 and 8. According to this embodiment, the effect of sterilization of the mouth portion of the preform by the disinfectant blown thereto can be improved, and poor sterilization of the mouth portion can be eliminated.

(Summary of Heating Apparatus for Preforms)

Figure 1:
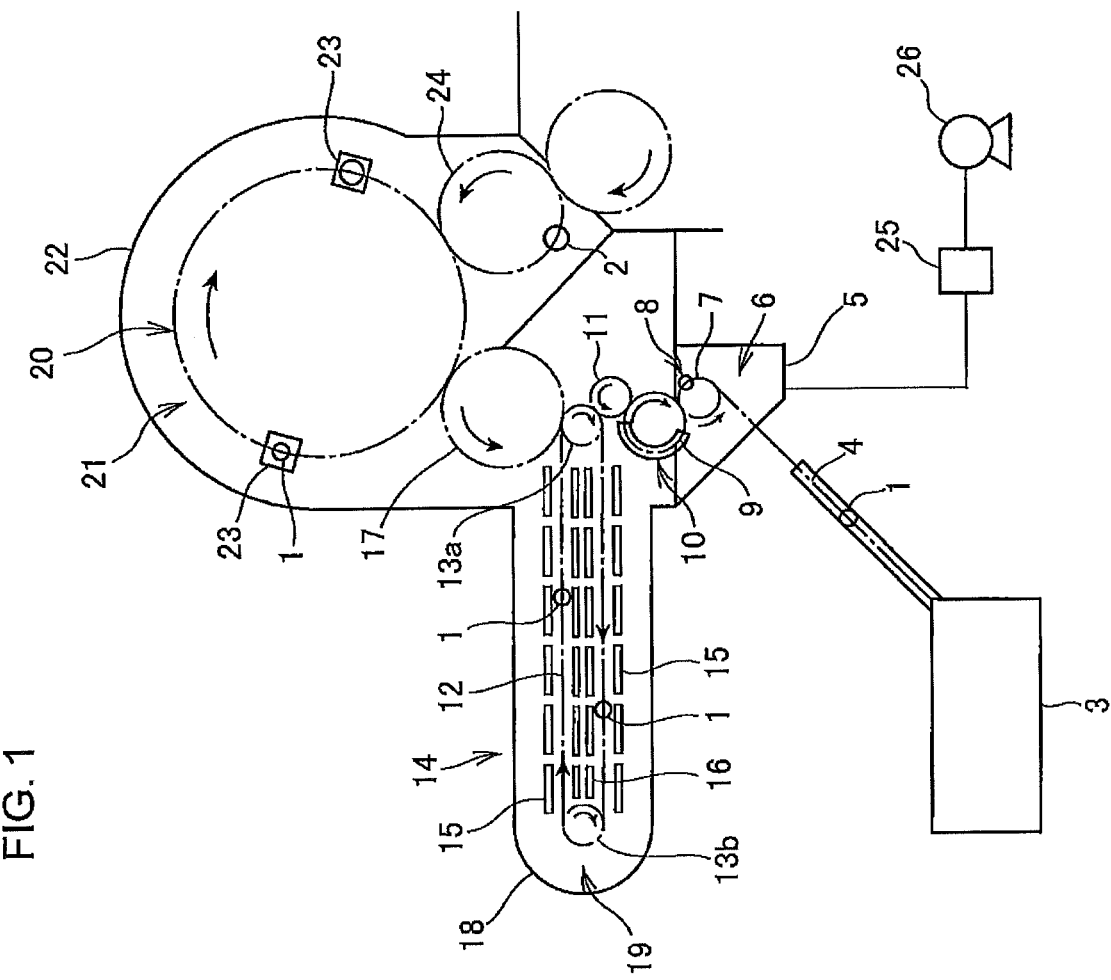
FIG. 1 shows a schematic plan view of a part of an aseptic filling machine incorporating a heating apparatus for preforms according to an embodiment of the present invention.
Figure 2:
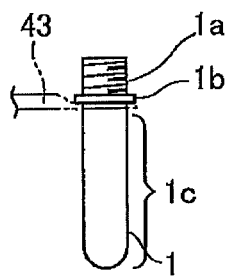
FIG. 2 illustrates a preform supply step according to the embodiment of the present invention.
Figure 10:
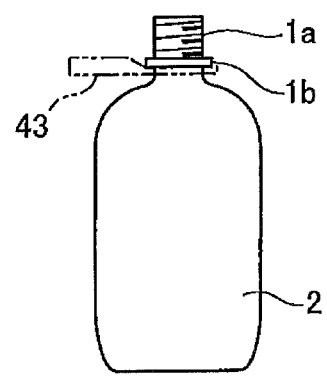
FIG. 10 illustrates a step of removing a bottle according to the embodiment of the present invention.

A heating apparatus 14 for preforms according to the present invention is an apparatus that heats a preform 1 shown in FIG. 2 to a temperature at which the preform 1 is molded into a bottle 2 shown in FIG. 10. As shown in FIG. 2, the preform 1 includes a mouth portion 1a, a support ring 1b, and a body portion 1c. As shown in FIG. 1, the preform 1 is supplied from a preform supplying apparatus 3, and the supplied preform 1 is sterilized in a sterilizing unit 6. The sterilized preform 1 is heated by the heating apparatus 14 for preforms according to the present invention to a temperature at which the preform 1 can be molded, and the heated preform 1 is passed to a blow molding machine 20. The heating apparatus 14 for preforms according to the embodiment of the present invention includes a heating section 19 and a driving unit 28, and the heating section 19 includes a mouth portion heating section 30 that heats the mouth portion of the preform 1 and a body portion heating section 29 that heats the body portion of the preform 1. The mouth portion heating section 30 and the body portion heating section 29 each include a heater 15, a reflector 16, a spindle 27, an endless chain 12, and a pulley 13 for rotating the endless chain 12, for example. The endless chain 12 is provided with the spindles 27 at regular intervals, and the sterilized preform 1 is held and rotated by the spindle 27, and heated by the heater 15 to a temperature at which the preform 1 can be molded. The mouth portion 1a and the support ring 1b of the preform 1 are heated by the mouth portion heating section 30, and the body portion 1c of the preform 1 is heated by the body portion heating section 29. The mouth portion 1a and the support ring 1b of the preform. 1 are heated by the mouth portion heating section 30 to a temperature from 50° C. to 70° C., and the body portion 1c of the preform 1 is heated by the body portion heating section 29 to a temperature from 90° C. to 140° C.

The preform 1 heated by the heating apparatus 14 for preforms is molded into a bottle 2 in a molding unit 21, and the molded bottle 2 is sequentially conveyed to an inspection unit that inspects the bottle 2, a filling unit that fills the inspected bottle 2 with a sterilized content, and further a sealing unit that seals the bottle 2 filled with the content with a sterilized cap. In this way, an aseptic product filled with the content is provided.

The heating section 19 of the heating apparatus 14 for preforms is covered by a heating section chamber 18, and before operating the heating apparatus 14 for preforms, the inside of the heating section chamber 18 is sterilized, an aseptic air is thereafter supplied into the heating section chamber 18, and the inside of the heating section chamber 18 is maintained at a positive pressure, and thus the preform 1 is heated to the temperature at which the preform 1 can be molded into the bottle 2 in a state where the sterility of the sterilized preform 1 is maintained.

Since the temperature in the heating section chamber 18 is relatively high, and the mouth portion 1a of the preform 1 is blocked by the spindle 27, the possibility that the preform 1 is contaminated with bacteria or the like in the heating section chamber 18 is low, so that the inside of the heating section chamber 18 may not be sterilized before operating the heating apparatus 14.

In order to sterilize the inside of the heating section chamber 18, a sterilizing apparatus is provided in the heating section chamber 18. Additionally, in order to maintain the inside of the heating section chamber 18 at a proper positive pressure by supplying an aseptic air, the heating section chamber 18 is provided with an aseptic air supplying apparatus 31 and an exhaust apparatus 37.

The inside of a molding unit chamber 22 that covers the molding unit 21, an inspection unit chamber that covers the inspection unit, and a filling unit chamber that covers the filling unit and the sealing unit is also sterilized before the operation of the aseptic filling machine, and the inside of the chambers is maintained at a positive pressure with an aseptic air, thereby maintaining the sterility in the chambers. Of the positive pressures maintained in the chambers, the pressure in the filling unit chamber is the highest, and the pressures in the inspection unit chamber, the molding unit chamber 22 and the heating section chamber 18 are set to be lower than the pressure in the filling unit chamber.

For example, the pressure in the filling unit chamber is 30 Pa to 150 Pa, and the pressure in the inspection unit chamber is set to 30 Pa to 100 PA. The pressure in the molding unit chamber is set to 20 Pa to 100 Pa, and the pressure in the heating section chamber 18 is set to 10 Pa to 50 Pa. Further, an exit chamber, which is located downstream from the sealing unit and in which the aseptic product is placed on a conveyor for discharge to the outside of the aseptic filling machine, is a non-aseptic zone, and is exhausted and set to −30 Pa to 30 Pa.

Although an aseptic air supplying apparatus is provided in order to maintain the inside of each chamber at a positive pressure, it is not necessary for all of the heating section chamber 18, the molding unit chamber 22, the inspection unit chamber, and the filling unit chamber to be provided with an aseptic air supplying apparatus. For example, the aseptic air supplied by the aseptic air supplying apparatus provided for the filling unit chamber may flow from the filling unit chamber into the inspection unit chamber and then into the molding unit chamber 22, and the inside of the molding unit chamber 22 may be maintained at a positive pressure by the inflow aseptic air. The exhaust apparatus, which is provided to maintain the inside of the chamber at a proper pressure, may not also be provided for all of the heating section chamber 18, the molding unit chamber 22, the inspection unit chamber, and the filling unit chamber.

A sterilizing unit chamber 5 that covers the sterilizing unit 6 that sterilizes the preform 1 is connected to an exhaust device, which is formed by a filter 25 that dissolves the disinfectant in the air in the sterilizing unit chamber 5 and a blower 26. By exhausting the air in the sterilizing unit chamber 5 during operation of the sterilizing unit 6, the inflow of the disinfectant to the adjacent heating section 19 can be prevented. Since the sterilizing unit chamber 5 is exhausted, the pressure in the sterilizing unit chamber 5 is set to −20 Pa to 20 Pa.

(Details of Heating Apparatus for Preforms and Heating Method for Preforms)

First, a preform 1 shown in FIG. 2 is continuously conveyed on a preform supplying conveyor 4 from the preform supplying apparatus 3 shown in FIG. 1 to the sterilizing unit 6 for the preforms 1 at a desired speed.

The preform 1 in this embodiment is a test tube-like bottomed tubular body, and has a mouth portion 1a, which is similar to that of the bottle 2 shown in FIG. 10, formed at an early stage of the molding thereof. A male thread is formed in the mouth portion 1a simultaneously with the molding of the preform 1. Additionally, a support ring 1b for conveyance is formed below the mouth portion 1a of the preform 1. The preform 1 or the bottle 2 is conveyed in the sterilizing unit 6 with the support ring 1b gripped by a gripper 43. The preform 1 further has a body portion 1c, which will form the body portion of the bottle after the preform 1 is molded into the bottle, below the support ring 1b. The preform 1 is molded by injection molding or compression molding, for example. The preform 1 may be made of a thermoplastic resin, such as polyethylene terephthalate, polyethylene naphthalate, polypropylene, and polyethylene. The preform 1 may be made of one of, or a mixture of, these thermoplastic resins, and may contain a recycled thermoplastic resin. Additionally, in order to provide a barrier property, the preform 1 may contain, in the form of a layer or as an admixture, a thermoplastic resin such as an ethylene-vinylalcohol copolymer or a polyamide having aromatic amine such as meta-xylenediamine as a monomer.

The preform 1 is passed from the preform supplying conveyor 4 to a preform sterilization wheel 7 by being gripped by one of grippers 43 provided at regular intervals on the preform sterilization wheel 7. In order to sterilize the preform 1, a sterilization apparatus 8 blows a gas or mist of a disinfectant or a mixture thereof to the inner and outer surfaces of the passed preform 1. The bacteria or the like adhering to the surfaces of the preform 1 are sterilized by the disinfectant blown to the preform 1.

Figure 3:
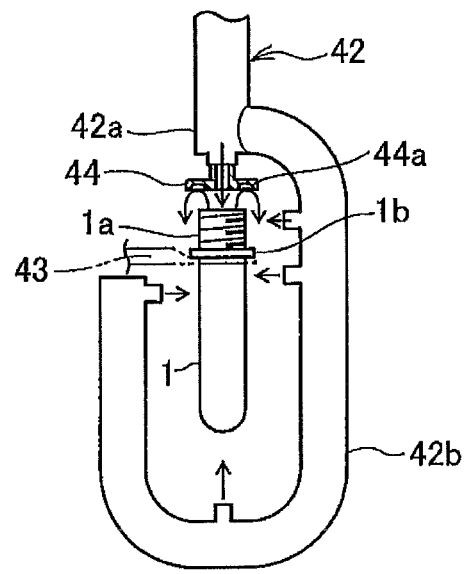
FIG. 3 illustrates a step of blowing disinfectant gas to a preform according to the embodiment of the present invention.

The gas or mist of the disinfectant or the mixture thereof is a part of the gas of the disinfectant that is generated by a disinfectant gas generator 39 shown in FIG. 4 described later and then turned into mist. The sterilization apparatus 8 is a disinfectant gas blowing nozzle 42 shown in FIG. 3, and the disinfectant gas blowing nozzle 42 blows the gas or mist of the disinfectant or the mixture thereof to the preform 1. The gas of the disinfectant is divided into two flows in the disinfectant gas blowing nozzle 42, one of the flows is blown into the preform 1 from a nozzle 42a, and the other flow is blown to the outer surface of the preform 1 from another nozzle 42b. The gas of the disinfectant may flow into the preform 1 or come into contact with the outer surface of the preform 1 as a gas or a mist or a mixture thereof after coming out of the disinfectant gas blowing nozzle 42.

The gas or mist of the disinfectant or the mixture thereof blown into the preform 1 flows into the preform 1 and then overflows from the mouth portion 1a of the preform 1. The overflow gas of the disinfectant or the like collides with an umbrella-like member 44, changes the direction toward the outer surface of the preform 1 by being guided by the inner surface of the umbrella-like member 44, and then comes into contact with the outer surface of the preform 1. If an annular groove 44a is formed in the umbrella-like member 44, the overflow gas of the disinfectant or the like flows along the outer surface of the preform 1. A separate nozzle may be provided to blow the gas or mist of the disinfectant or the mixture thereof directly to the outer surface of the preform 1. Any device may be used as far as the gas or mist of the disinfectant or the mixture thereof can come into contact with the inner and outer surfaces of the preform 1.

Figure 4:
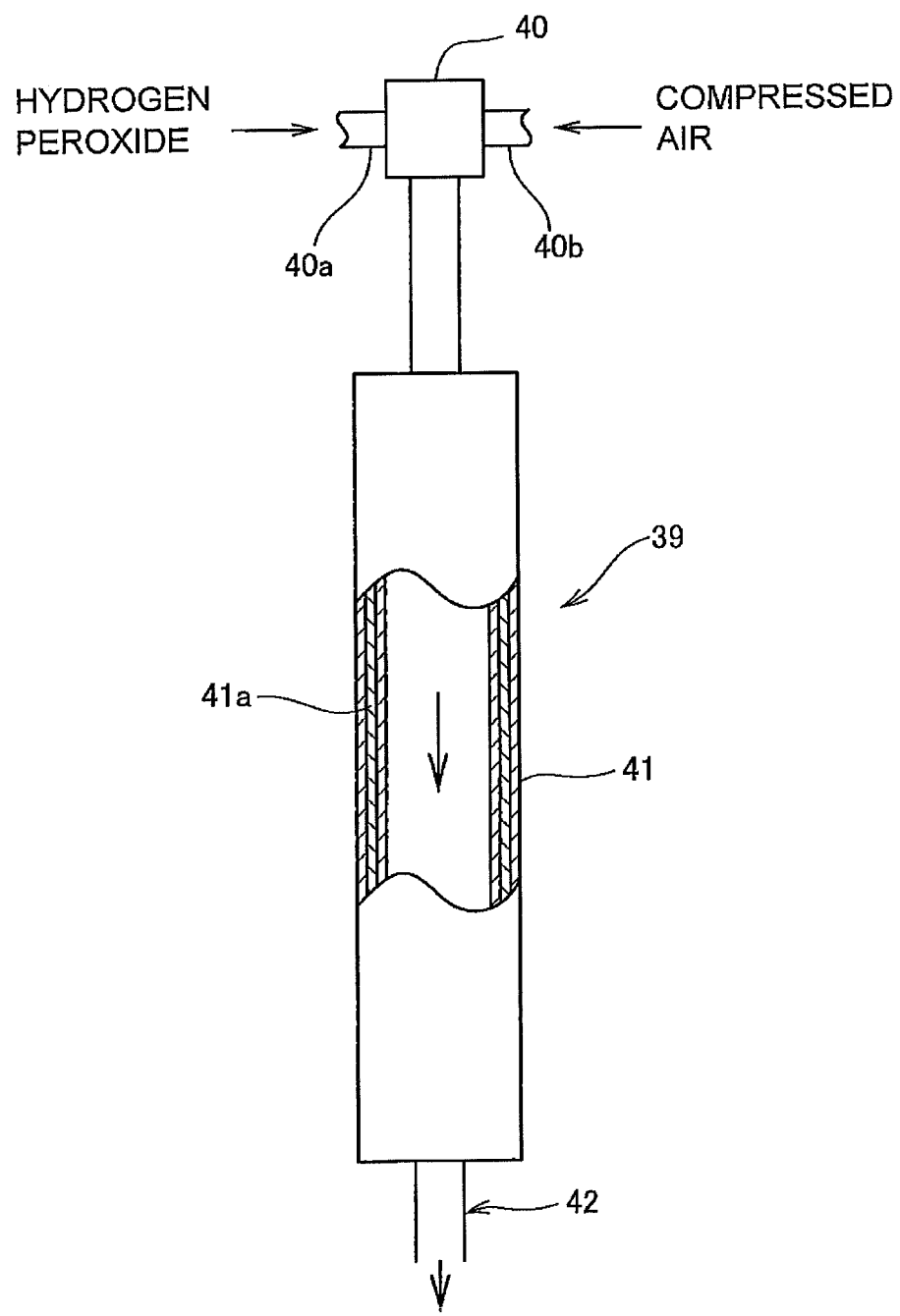
FIG. 4 shows a disinfectant gas generator according to the embodiment of the present invention.

As shown in FIG. 4, the disinfectant gas generator 39 includes a disinfectant supplying unit 40 that is a two-fluid spray nozzle supplying the disinfectant in drops, and a vaporizing unit 41 that heats the disinfectant supplied from the disinfectant supplying unit 40 to a dissolution temperature or less to vaporize the disinfectant. The disinfectant supplying unit 40 takes in the disinfectant and compressed air from a disinfectant supply path 40a and a compressed air supply path 40b, respectively, and sprays the disinfectant into the vaporizing unit 41. The vaporizing unit 41 is a pipe that incorporates a heater 41a interposed between inner and outer walls thereof, and heats and vaporizes the disinfectant blown into the pipe. The gas of the vaporized disinfectant is ejected to the outside of the vaporizing unit 41 from a lower end of the vaporizing unit 41. The vaporizing unit 41 may be heated by induction heating instead of the heater 41a.

As for the operating condition of the disinfectant supplying unit 40, for example, the pressure of the compressed air is adjusted in the range of 0.05 MPa to 0.6 MPa. Additionally, the disinfectant may fall down by gravity or under pressure, and the supply amount can be arbitrarily set. For example, the disinfectant is supplied in the range of 1 g/min to 100 g/min. Additionally, the sprayed disinfectant is vaporized by heating the inner surface of the vaporizing unit 41 to a temperature of 140° C. to 450° C.

Although the blowing amount of the gas or mist of the disinfectant or the mixture thereof is arbitrary, the blowing amount is determined by the amount of the disinfectant supplied to the disinfectant gas generator 39 and the blowing time. A plurality of disinfectant gas generators 39 may be provided. When the disinfectant is a hydrogen peroxide solution, a proper range of the concentration of hydrogen peroxide is 1 mg/L to 20 mg/L. When the concentration is less than 1 mg/L, the sterilization is insufficient, and when the concentration is higher than 20 mg/L, there is a possibility that an excessive amount of hydrogen peroxide remains in the molded bottle 2.

The preform 1 may be pre-heated by blowing hot air to the preform 1, for example, immediately before blowing the gas or mist of the disinfectant or the mixture thereof to the preform 1. The pre-heating can further increase the effect of sterilization of the preform 1.

The disinfectant blown to the preform 1 preferably contains at least hydrogen peroxide. A proper range of the content is 0.5 mass % to 65 mass %. When the content is less than 0.5 mass %, the sterilizing power may be insufficient, and when the content is higher than 65 mass %, the disinfectant is difficult to handle safely. A more preferable range is 0.5 mass % to 40 mass %, and when the content is 40 mass % or less, the disinfectant is more easy to handle, and the residual amount of hydrogen peroxide after sterilization can be reduced because of its lower concentration.

When the disinfectant blown to the preform 1 contains hydrogen peroxide, the amount of the disinfectant adhering to the inner and outer surfaces of the preform 1 is preferably in the range of 0.001 $\mu L/cm^2$ to 0.5 $\mu L/cm^2$ on the assumption that the disinfectant is a hydrogen peroxide solution containing 35 mass % of hydrogen peroxide. When the adhering amount is less than 0.001 $\mu L/cm^2$, a sufficient sterilizing effect cannot be obtained. When the adhering amount is higher than 0.5 $\mu L/cm^2$, defective molding is likely to occur in the bottle 2, such as bleaching, a spot, a wrinkle, and deformation, when the preform 1 is blow-molded into the bottle 2. More preferably, the amount of the hydrogen peroxide solution containing 35 mass % of hydrogen peroxide adhering to the preform 1 is 0.002 $\mu L/cm^2$ to 0.4 $\mu L/cm^2$.

Although the disinfectant contains water, the disinfectant may contain one or two or more of alcohols such as methyl alcohol, ethyl alcohol, isopropyl alcohol, normal propyl alcohol, and butyl alcohol, ketones such as acetone, methyl ethyl ketone, and acetylacetone, and glycol ether, for example.

Further, the disinfectant may contain an organic acid such as peracetic acid and acetic acid, a chlorine compound such as sodium hypochlorite, an alkaline compound such as sodium hydroxide and potassium hydroxide, a compound having the sterilizing effect such as nitric acid, ozone, and acid water, and an additive agent such as a cationic surfactant, a nonionic surfactant, and a phosphoric acid compound.

A light irradiation apparatus or an electron beam irradiation apparatus may be provided as a part of the sterilization apparatus 8, and before or after blowing of the disinfectant, the preform 1 may be irradiated with light containing an ultraviolet radiation having a wavelength of 100 nm to 380 nm or an electron beam or the like to improve the sterilizing effect.

Before operating the aseptic filling machine, the inside of the sterilizing unit chamber 5 is sterilized by spraying the disinfectant such as a hydrogen peroxide solution into the sterilizing unit chamber 5, for example. To this end, in addition to the disinfectant gas blowing nozzle 42 for blowing the gas or mist of the disinfectant or the mixture thereof to the preform 1, a disinfectant blowing nozzle is provided on an inner wall surface of the sterilizing unit chamber 5. Additionally, a similar disinfectant blowing nozzle is also provided to sterilize a surface on the side of the sterilizing unit chamber 5 of a filter 25 adjacent to the sterilizing unit chamber 5.

The preform 1 to which the gas or mist of the disinfectant or the mixture thereof has been blown is passed to an air blowing wheel 9 as shown in FIG. 1. The preform 1 passed to the wheel 9 is conveyed by the gripper 43 through an aseptic air blowing tunnel 10, and an aseptic air is blown to the preform 1. The aseptic air is produced by passing air from a blower through an aseptic filter. The blower may not be used, and compressed air generated by a compressor may be sterilized through an aseptic filter and used.

The aseptic air blowing tunnel 10 covers the mouth portion 1a of the preform 1 from above, and has a ceiling part shaped like a roof having an inclined face. In the ceiling part, a preform aseptic air supply nozzle that blows the aseptic air to the mouth portion 1a of the preform 1 is provided in the form of a row of pipes or a slit. In this way, the aseptic air is efficiently supplied to the preform 1.

By blowing the aseptic air, the disinfectant adhering to the surface of the preform 1 is activated, and any bacteria or the like having survived the blowing of the disinfectant to the preform 1 may be killed. Additionally, by blowing the aseptic air, the disinfectant adhering to the preform 1 is quickly removed from the surface of the preform 1. Since the disinfectant adhering to the preform 1 is removed from the preform 1 by the blowing of the aseptic air before the preform 1 enters the heating section 19, various pieces of equipment such as a sealing member of the heating section 19 is not damaged by the disinfectant. Additionally, the occurrence of defective molding of the bottle, such as bleaching, distortion, and uneven molding, caused by the disinfectant adhering to the preform 1 is prevented.

The aseptic air blown to the preform 1 may be at room temperature or may be heated. However, the aseptic air is preferably heated. The aseptic hot air produced by heating the aseptic air promotes the dissolution of the disinfectant to increase the sterilizing effect, and reduces the residual of the disinfectant. The temperature of the aseptic hot air blown to the preform 1 is desirably from 40° C. to 140° C. When the temperature is less than 40° C., the effect of the heating is insufficient. The temperature of the hot air is desirably not higher than 140° C. because a problem such as deformation of the mouth portion 1a of the preform 1 can occur if the temperature of preform 1 is higher than 70° C. when the temperature of the hot air is higher than 140° C.

The blowing of the aseptic air to the preform 1 is not essential and may not be performed. When the blowing of the aseptic air is not performed, the preform 1 is directly heated after the gas of the disinfectant is blown to the preform 1. The disinfectant is adhering to the inner and outer surfaces of the preform 1 to which the gas of the disinfectant has been blown, and when the preform 1 is heated to the molding temperature, the adhering disinfectant is activated to sterilize the surface of the preform 1. Any excess disinfectant is vaporized by the heating.

After blowing of the aseptic air, the preform 1 is passed to a heating furnace conveyance wheel 11 shown in FIG. 1. At the wheel 11, the preform 1 is released from the gripper 43, the spindle 27 is inserted into the mouth portion 1a of the preform 1 as shown in FIG. 5, and the preform 1 is conveyed into the heating section 19 by the endless chain 12.

Figure 6:
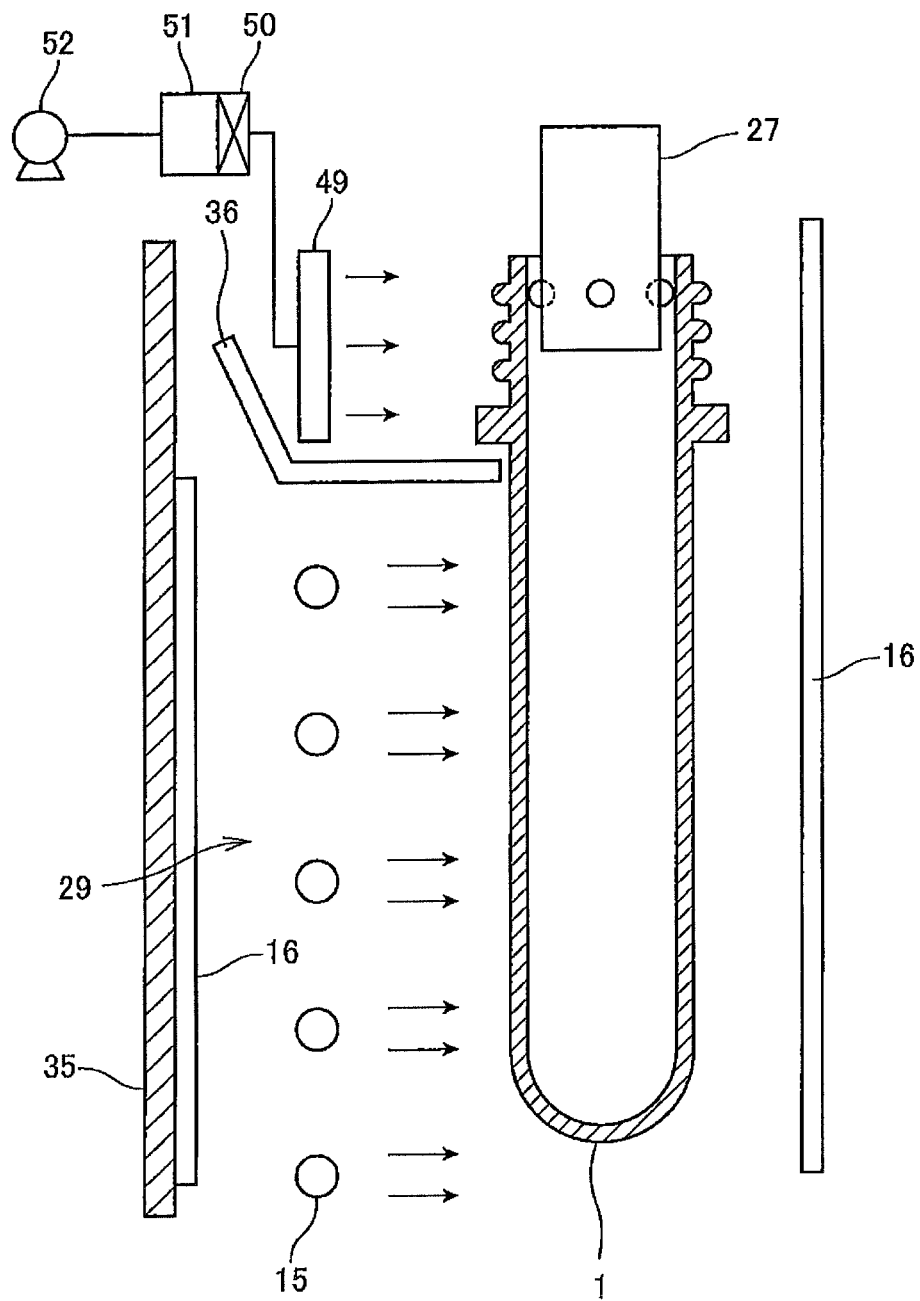
FIG. 6 illustrates a step of heating a body portion of the preform according to the embodiment of the present invention.
Figure 7:
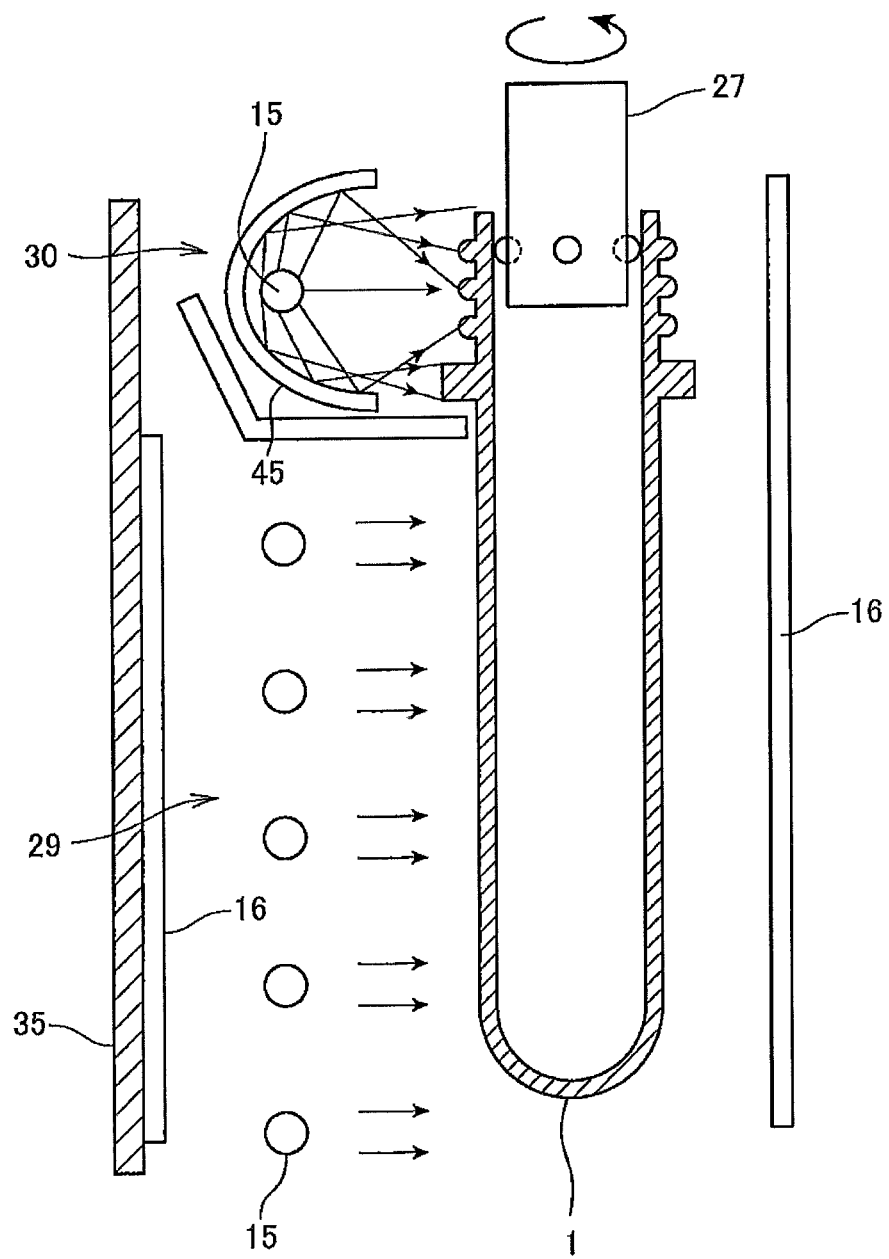
FIG. 7 illustrates a step of heating the mouth portion and the body portion of the preform according to the embodiment of the present invention.

The heating section 19 includes the mouth portion heating section 30 that heats the mouth portion 1a and the support ring 1b of the preform 1, and the body portion heating section 29 that heats the body portion 1c of the preform 1. The mouth portion heating section 30 is shown in FIG. 5. The body portion heating section 29 is shown in FIG. 6. FIG. 7 shows the heating section 19 provided with both the mouth portion heating section 30 and the body portion heating section 29. The combination of the mouth portion heating section 30 and the body portion heating section 29 can be arbitrarily chosen: the mouth portion heating section 30 may be provided in the early stage in the heating section 19 shown in FIG. 1, and the body portion heating section 29 may be provided for the n-th and following heaters 15 (n represents a positive integer); or both the mouth portion heating section 30 and the body portion heating section 29 may be provided from the early stage in the heating section 19, and only the body portion heating section 29 may be provided for the n-th and following heaters 15. Further, the mouth portion heating section 30 may be provided anywhere in the heating section 19. Preferably, both the mouth portion heating section 30 and the body portion heating section 29 are provided in the early stage in the heating section 19, and only the body portion heating section 29 is provided in the following section. If the body portion 1c is first heated, and the mouth portion 1a is then heated, the mouth portion 1a can also be heated when the body portion 1c is heated, and it can be difficult to control the temperature of the mouth portion 1a when heating the mouth portion 1a.

Figure 5:
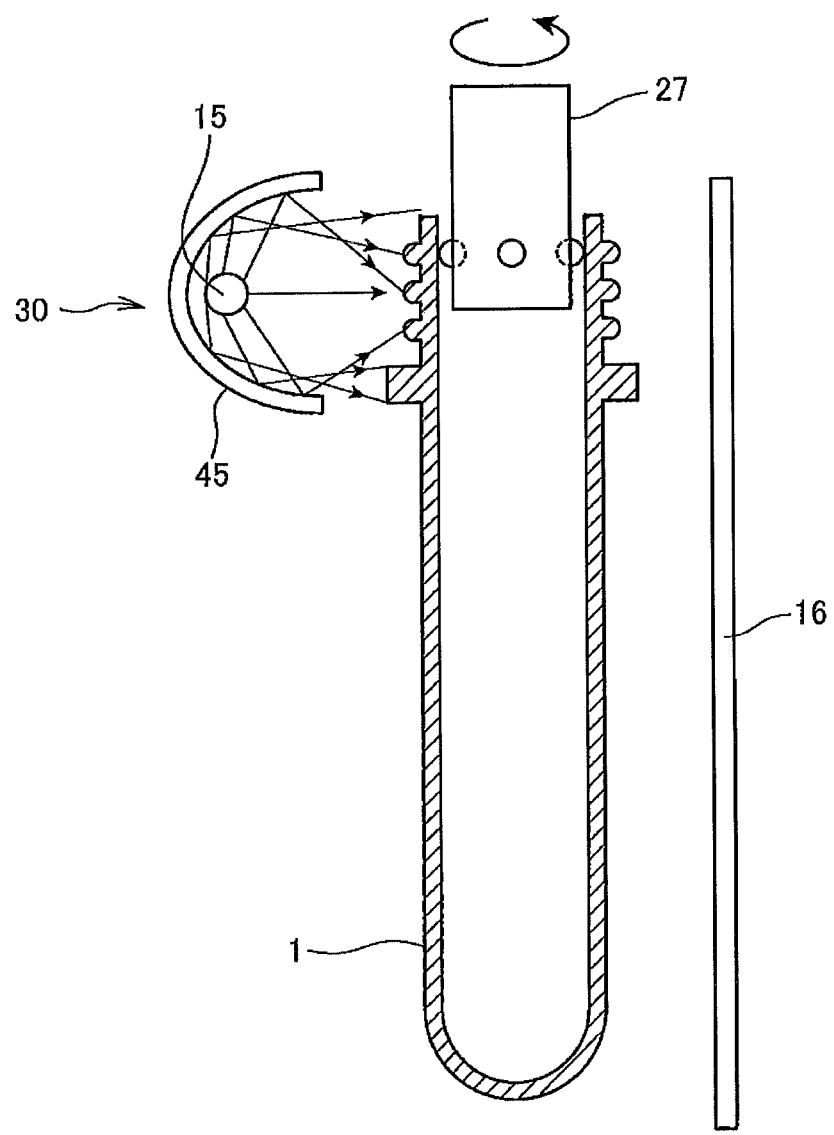
FIG. 5 illustrates a step of heating a mouth portion of the preform according to the embodiment of the present invention.

As shown in FIG. 5, the mouth portion heating section 30 is provided with mouth portion heating equipment, which is formed by the heater 15 and a condenser 45. The heater 15 is preferably a halogen lamp that emits near infrared radiation or the like. Any near infrared radiation or the like that is not absorbed by the preform 1 and goes beyond the preform 1 does not contribute to heating. In view of this, as shown in FIG. 5, if a reflector 16 is provided behind the preform 1, any near infrared radiation or the like going beyond the preform 1 can be reflected to efficiently heat the preform 1. The preform 1 is heated by the near infrared radiation, infrared radiation and the far infrared radiation emitted from the halogen lamp of the heater 15. The heater 15 has a rod-like shape and is provided perpendicularly to the axial direction of the preform 1.

Further, the condenser 45 is provided which reflects the near infrared radiation or the like emitted from the heater 15 and efficiently heats the mouth portion 1a and the support ring 1b of the preform 1. The condenser 45 has a dome-like shape and covers the heater 15. The condenser 45 is configured to reflect the other near infrared radiation or the like than the near infrared radiation or the like emitted from the heater 15 and traveling straight to the mouth portion 1a and the support ring 1b of the preform 1 and directs the near infrared radiation or the like to the mouth portion 1a and the support ring 1b of the preform 1. The condenser 45 is made of a metal and coated with gold, silver or aluminum by vapor deposition or plating. The condenser may have any shape and may have a curved surface or a combination of a planer surface and a curved surface as far as the condenser can reflect the near infrared radiation or the like in a desired direction.

The mouth portion 1a and the support ring 1b of the preform 1 are heated to a temperature from 50° C. to 70° C. by the mouth portion heating section 30. At temperatures less than 50° C., the disinfectant on the preform 1 can be insufficiently activated, and the mouth portion 1a and the support ring 1b of the preform 1 can be poorly sterilized. At temperatures higher than 70° C., the mouth portion 1a of the preform 1 can be deformed, and the bottle 2 molded from the preform 1 can be poorly sealed with a cap when the cap is fitted to the bottle 2.

As shown in FIG. 5, the spindle 27 is inserted into the mouth portion 1*a*, and the preform 1 is conveyed in the heating section 19 while being rotated. The preform 1 is held on the spindle 27 by elastic deformation of an elastic body such as a rubber or a spring when a lower part of the spindle 27 is inserted into the mouth portion 1*a*. The spindle 27 is held on the endless chain 12. The endless chain 12 is rotated by pulleys 13*a* and 13*b*. Instead of the spindle 27, a mandrel may be inserted into the preform 1 to convey the preform 1 while rotating the preform 1 in an inverted state.

The body portion heating section 29 shown in FIG. 6 includes body portion heating equipment formed by the heater 15 and the reflector 16, for example. A plurality of heaters 15 arranged perpendicularly to the axial direction of the preform 1 are provided in parallel. The heating temperature of the plurality of halogen lamps is controlled, and the heating temperature may vary in the axial direction of the body portion 1*c* of the preform 1. In the direction of travel of the preform 1, a plurality of halogen lamp units as the heaters 15 are provided as shown in FIG. 1. Although FIG. 1 shows a total of 12 units, two rows of six units, some of the units of the heaters 15 may serve as the mouth portion heating section 30, as the body portion heating section 29, or as both the mouth portion heating section 30 and the body portion heating section 29. For example, the first three halogen lamp units may serve as the mouth portion heating section 30, and the fourth to twelfth halogen lamp units may serve as the body portion heating section. The number of halogen lamp units can be arbitrarily determined, and may be smaller or greater than 12.

As shown in FIG. 6, the body portion heating section 29 is provided with the reflector 16 in the same manner as the mouth portion heating section 30. The body portion heating section 29 is further provided with the reflector 16 on the opposite side of the heaters 15 to the preform 1. Further, in order to prevent the heat from the heaters 15 from being transmitted to the outside of the heating apparatus 14 for preforms, a heat insulation material 35 may be provided on the outer side of the heaters 15. The reflector 16 has the same configuration as the condenser 45 and may have a planar or curved surface.

The body portion 1*c* of the preform 1 is heated to a temperature from 90° C. to 140° C. by the body portion heating section 29. At temperatures less than 90° C., the preform 1 is poorly shaped in a molding die 23 when the preform 1 is blow-molded into the bottle 2. At temperatures higher than 140° C., the thickness of the bottle 2 can be uneven.

The body portion heating section 29 is provided with a mouth portion protection member 36 shown in FIG. 6 in order to prevent the mouth portion 1*a* and the support ring 1*b* from being heated to temperatures higher than 70° C. by the heat for heating the body portion 1*c* of the preform 1. The mouth portion protection member 36 is provided below the support ring 1*b* of the preform 1 so as to have a surface perpendicular to the axial direction of the preform 1. The mouth portion protection member 36 prevents the near infrared radiation or the like emitted from the heaters 15 of the body portion heating section 29 from reaching the mouth portion 1*a* and the support ring 1*b* of the preform 1. Additionally, in order to prevent the temperature of the mouth portion 1*a* from rising because of the ascending air current generated by the heat from the heaters 15 of the body portion heating section 29, a tip end part of the mouth portion protection member 36 closer to the heaters 15 may be angled by 90° or less with respect to the axial direction of the preform 1, as shown in FIG. 6. The mouth portion protection member 36 is preferably cooled by circulating a cooling medium such as water in the mouth portion protection member 36.

Further, in order to prevent the temperature of the mouth portion 1*a* of the preform 1 from rising because of the ascending air current generated by the heat from the heaters 15 of the body portion heating section 29, the body portion heating section 29 may be provided with a cold air blowing nozzle 49 for blowing the cold air to the mouth portion 1*a* as shown in FIG. 6, and cold air may be blown to the mouth portion 1*a*. The preform 1 is rotated while being conveyed on the endless chain 12, so that the temperature of the mouth portion 1*a* can be prevented from rising by blowing cold air from one direction. The cold air is preferably blown from the side opposite to the reflector 16. Air from a blower 52 is cooled by a cooling apparatus 51 and passed through an aseptic filter 50, and the resulting air is blown from the cold air blowing nozzle 49 to the mouth portion 1*a* of the preform 1. The cooling apparatus 51 may not be provided, and air at room temperature may be blown.

FIG. 7 shows a heating unit provided with both the mouth portion heating section 30 and the body portion heating section 29. For example, three such heating units may be provided in an early stage in the heating section 19 shown in FIG. 1, and only the body portion heating section 29 may be provided in the following section. Alternatively, three such heating units may be provided in a final stage in the heating section 19.

Figure 8:
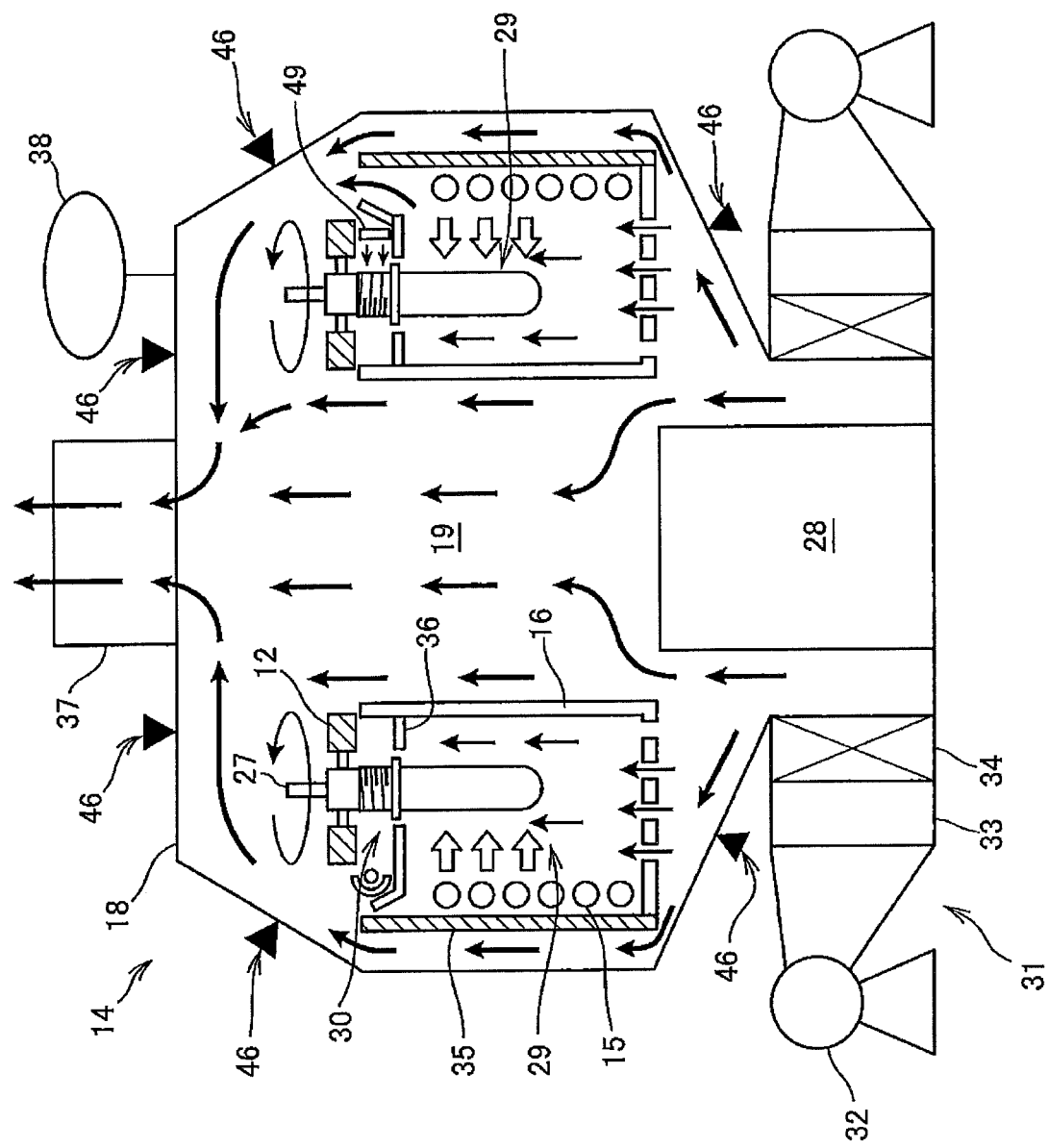
FIG. 8 is a schematic cross-sectional view of an example of a heating apparatus according to the embodiment of the present invention.

FIG. 8 is a cross-sectional view of the heating apparatus 14 for preforms. The left half of the drawing shows an early stage in the heating section 19, in which both the mouth portion heating section 30 and the body portion heating section 29 are provided. The right half of the drawing shows a final stage in the heating section 19, in which only the body portion heating section 29 is provided. The heating apparatus 14 for preforms have at least the heating section 19 and the driving unit 28. The driving unit 28 is provided with a motor or a motion transmission device, for example. The equipment of the driving unit 28 requires lubricant and gets dirty over time, so that it is difficult to keep the sterility of the equipment.

The heating section 19 of the heating apparatus 14 for preforms is covered by the heating section chamber 18, and before operating the heating apparatus 14 for preforms, the inside of the heating section chamber 18 is preferably sterilized. After that, an aseptic air is supplied into the heating section chamber 18, and the inside of the heating section chamber 18 is maintained at a positive pressure. In this way, the preform 1 is heated to a temperature at which the preform 1 can be molded into the bottle 2 in a state where the sterility of the sterilized preform 1 is maintained.

In order to sterilize the inside of the heating section chamber 18, the heating section chamber 18 is provided with a sterilizing apparatus. Additionally, in order to maintain the inside of the heating section chamber 18 at a proper pressure, the aseptic air supplying apparatus 31 and the exhaust apparatus 37 are provided.

The heating section chamber 18 is provided with the sterilizing apparatus in order to sterilize the inside of the heating section chamber 18 before operating the heating apparatus 14 for preforms. The sterilizing apparatus is a disinfectant nozzle 46 that blows the gas or mist of the disinfectant or the mixture thereof into the heating section chamber 18 and the disinfectant gas generator 39 that generates the gas of the disinfectant, for example.

As shown in FIG. 8, the disinfectant nozzle 46 is provided on a wall of the heating section chamber 18, and the gas or mist of the disinfectant or the mixture thereof is blown from the disinfectant nozzle 46 into the heating section chamber 18. From the disinfectant nozzle 46, the gas of the disinfectant generated by the disinfectant gas generator 39 shown in FIG. 4 is blown to the heating section 19 in the heating section chamber 18 and the wall surface in the heating section chamber 18. The disinfectant used and the generation conditions for the disinfectant gas are the same as the disinfectant used for sterilizing the preform 1 and the generation conditions for the gas or mist of the disinfectant or the mixture thereof.

The gas of the disinfectant generated by the disinfectant gas generator 39 shown in FIG. 4 is mixed with heated aseptic air, and the resulting gas or mist of the disinfectant or the mixture thereof is blown from the disinfectant nozzle 46 into the heating section chamber 18. Although the blowing amount of the gas or mist of the disinfectant or the mixture thereof is arbitrary, the blowing amount is determined by the amount of the disinfectant supplied to the disinfectant gas generator 39 and the blowing time. A plurality of disinfectant gas generators 39 may be provided. When the disinfectant is a hydrogen peroxide solution, a proper range of the concentration of hydrogen peroxide in the gas or mist of the disinfectant or the mixture thereof is 1 mg/L to 20 mg/L. When the concentration is less than 1 mg/L, the sterilization is insufficient, and when the concentration is higher than 20 mg/L, there is a possibility that members in the heating section chamber 18 are degraded. Additionally, the disinfectant may be turned into mist by the two-fluid spray, and may be blown into the heating section chamber 18 from the disinfectant nozzle 46. In that case, the mist of the disinfectant may be blown to the heater 15, and the disinfectant may be vaporized by the heat from the heater 15.

Additionally, the inside of the heating section chamber 18 can also be sterilized while reducing variations in the amount of the disinfectant adhering to the equipment of the heating section 19, by operating the heating section 19 while the gas or mist of the disinfectant or the mixture thereof is being blown into the heating section chamber 18. Specifically, by driving the spindles 27, the grippers 43, the endless chain 12, the pulleys 13a and 13b and other equipment in the heating section chamber 18, the disinfectant can be made to adhere uniformly over the whole of the surfaces of the equipment.

After the gas or mist of the disinfectant or the mixture thereof is blown into the heating section chamber 18 from the disinfectant nozzle 46, aseptic air is blown into the heating section chamber 18. The aseptic air vaporizes and removes any disinfectant remaining in the heating section chamber 18. In this step, the vaporizing disinfectant may also have the sterilizing effect.

In order to blow the aseptic air into the heating section chamber 18 from below, as shown in FIG. 8, the heating section chamber 18 is provided with the aseptic air supplying apparatus 31 at a lower part thereof. The aseptic air supplying apparatus 31 includes a blower 32 and an aseptic filter 34. The aseptic air may also be heated, and an aseptic air heating apparatus 33 is preferably provided between the blower 32 and the aseptic filter 34.

After the air from the blower 32 is heated by the aseptic air heating apparatus 33 and is disinfected by the aseptic filter 34, the resulting aseptic hot air is blown into the lower part of the heating section chamber 18. Although the aseptic air may not be heated, if the aseptic air is heated, the disinfectant is quickly removed, and the sterilizing effect of the disinfectant is increased. When the aseptic air is supplied into the heating section chamber 18 in order to maintain the sterility in the heating section chamber 18 during operation of the heating apparatus 14 for preforms, the aseptic air may not be heated.

In the sterilization of the inside of the heating section chamber 18 before operating the heating apparatus 14 for preforms, the inner surface of the aseptic filter 34 formed by a HEPA filter or the like is also sterilized since the gas or mist of the disinfectant or the mixture thereof is blown from the disinfectant nozzle 46.

Since the inside of the heating section chamber 18 is heated by the heaters 15, an ascending air current is generated. The aseptic air can flow more smoothly without causing turbulence in the heating section chamber 18 when the aseptic air flows in the same direction as the ascending air current than when the aseptic air flows from above to below. For this reason, the aseptic air is blown into the heating section chamber 18 upward from the lower part thereof. As shown in FIG. 8, the aseptic air blown into the lower part flows upward in the spaces on the outer and inner sides of the heaters 15 and the reflectors 16.

In order to efficiently heat the preform 1, the flowrate of the aseptic air flowing between the heaters 15 and the reflector 16 may be controlled by adjusting the area of openings in a plate provided below the preform 1. The cooling effect of the flow of the aseptic air between the heaters 15 and the reflector 16 may be reduced by heating the aseptic air.

As shown in FIG. 8, the exhaust apparatus 37 may be provided on top of the heating section chamber 18, and the aseptic air may be exhausted to the outside of the heating apparatus 14 for preforms, thereby properly maintaining the pressure in the heating section chamber 18. As shown in FIG. 8, a pressure sensor 38 is provided on top of the heating section chamber 18, and the pressure in the heating section chamber 18 is constantly measured. The blower 32 and the exhaust apparatus 37 are controlled based on the pressure measurement to properly maintain the pressure in the heating section chamber 18.

As shown in FIG. 1, the heated preform 1 is released from the spindle 27, passed to a gripper on a wheel 17, and conveyed to the blow molding machine 20. Aseptic air may be blown to the mouth portion 1a of the preform 1 on the wheel 17. The preform 1 is fed to the molding die 23 provided in the molding unit 21 of the blow molding machine 20, with the sterility thereof maintained.

The inside of the molding unit chamber 22 is sterilized with a disinfectant such as a hydrogen peroxide solution before operation of the blow molding machine 20, and aseptic air is supplied into the molding unit chamber 22 during operation of the blow molding machine 20, so that the sterility of the inside of the molding unit chamber 22 is maintained. In order to sterilize the inside of the molding unit chamber 22 with the disinfectant, a disinfectant nozzle for spraying the disinfectant is provided on a wall of the molding unit chamber 22, as with the heating section chamber 18. Since the sterility of the molding unit chamber 22 is maintained, the molded bottle 2 also has the sterility.

Figure 9:
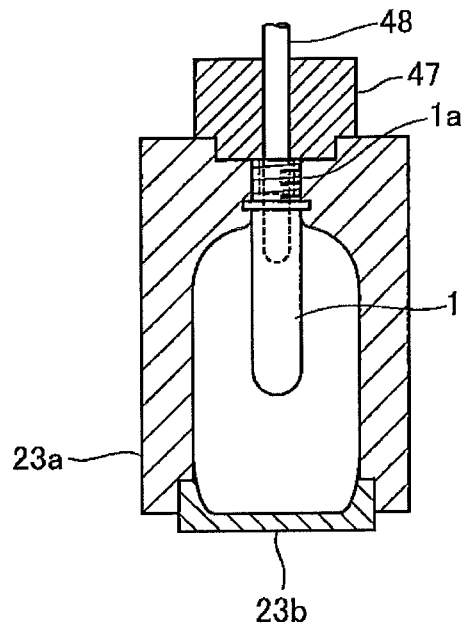
FIG. 9 illustrates a step of blow-molding the preform according to the embodiment of the present invention.

The preform 1 passed to the blow molding machine 20 is molded into the bottle 2 as shown in FIG. 9. The preform 1 is passed from the wheel 17 to the blow molding machine 20 by closing a split die 23a and a bottom die 23b of the molding die 23 together. After that, a blow nozzle 47 is joined to the mouth portion 1a of the preform 1, an extension rod 48 is guided by a hole in the blow nozzle 47 and inserted into the preform 1, and at the same time, an intermediate pressure air and a high pressure air are sequentially fed into the preform 1 by the action of an electromagnetic valve of a valve block, which is not shown, thereby molding the preform 1 into the bottle 2.

The bottle 2 molded by the blow molding machine 20 is removed from the molding die 23 by the gripper 43 and conveyed to the inspection unit chamber via a wheel 24, as shown in FIG. 10. The bottle 2 is inspected in the inspection unit chamber, and if the bottle 2 is determined to have no defect, the bottle 2 is conveyed to the filling unit chamber, filled with a sterilized content, sealed with a sterilized cap, and taken out into a non-aseptic atmosphere as an aseptic product. The inspection unit inspects the body, the top face of the mouth portion 1a, the support ring 1b, the bottom part and other parts of the bottle 2 for a foreign matter, a discoloration, a scratch or other defect. If the bottle 2 is determined to have such defects beyond a predetermined limit, the defective bottle 2 is discharged to the outside of the aseptic filling machine. The inspection may not be performed.

Although the present invention is configured as described above, the present invention is not limited to the embodiment described above, and various modifications can be made without departing from the spirit of the present invention.

REFERENCE SIGNS LIST

1 . . . preform
2 . . . bottle
5 . . . sterilizing unit chamber
12 . . . endless chain
13a, 13b . . . pulley
14 . . . heating apparatus for preforms
15 . . . heater
16 . . . reflector
18 . . . heating section chamber
19 . . . heating section
29 . . . body portion heating section
30 . . . mouth portion heating section
36 . . . mouth portion protection member
45 . . . condenser
49 . . . cold air blowing nozzle

The invention claimed is:

1. A heating apparatus for preforms that heats a preform to a temperature for blow-molding the preform into a bottle, the heating apparatus comprising:
a mouth portion heating section that heats a mouth portion of the preform; and
a body portion heating section that heats a body portion of the preform,
wherein the mouth portion heating section includes mouth portion heating equipment that heats the mouth portion to a temperature in a range of 50° C. to 70° C.,
wherein an early stage in the heating apparatus for preforms comprises the mouth portion heating section and the body portion heating section, and a final stage in the heating apparatus comprises the body portion heating section and a cold air blowing nozzle, and
wherein the cold air blowing nozzle has a flat shape facing the mouth portion of the preform.

2. The heating apparatus for preforms according to claim 1, wherein the body portion heating section includes body portion heating equipment that heats the body portion to a temperature in a range of 90° C. to 140° C.

3. The heating apparatus for preforms according to claim 1, wherein the mouth portion heating equipment includes a halogen lamp and a condenser that collects near infrared radiation emitted from the halogen lamp to the mouth portion.

4. A heating method for preforms comprising:
providing a preform to which a disinfectant containing hydrogen peroxide has been blown; and
heating the preform to a temperature for blow-molding the preform into a bottle,
wherein a mouth portion of the preform is heated to a temperature in a range of 50° C. to 70° C.,
wherein the mouth portion and a body portion of the preform are heated in an early stage of heating the preform,
wherein the body portion is heated and the mouth portion of the preform is blown with cold air in a final stage of heating the preform, and
wherein the cold air is blown from a cold air blowing nozzle having a flat shape facing the mouth portion of the preform.

5. The heating method for preforms according to claim 4, wherein a body portion of the preform is heated to a temperature in a range of 90° C. to 140° C.

6. The heating method for preforms according to claim 4, wherein the heating of the mouth portion is achieved by collecting near infrared radiation emitted from a halogen lamp to the mouth portion of the preform.

7. The heating apparatus for preforms according to claim 2, wherein the mouth portion heating equipment includes a halogen lamp and a condenser that collects near infrared radiation emitted from the halogen lamp to the mouth portion.

8. The heating method for preforms according to claim 5, wherein the heating of the mouth portion is achieved by collecting near infrared radiation emitted from a halogen lamp to the mouth portion of the preform.

* * * * *